United States Patent [19]

Mandai et al.

[11] Patent Number: 5,767,297
[45] Date of Patent: Jun. 16, 1998

[54] TAXOID DERIVATIVE AND METHOD OF PRODUCING THEREOF

[75] Inventors: Tadakatsu Mandai; Hiroshi Okumoto, both of Kurashiki; Koji Hara, Yokohama; Katsuhiko Mikuni, Yokohama; Kozo Hara, Yokohama; Hiroki Hamada, Okayama, all of Japan

[73] Assignees: Ensuiko Sugar Refining Co., Ltd., Yokohama; Tadakatsu MANDAI, Kurashiki; Kaken Pharmaceutical Co., Ltd., Tokyo, all of Japan

[21] Appl. No.: 868,151

[22] Filed: Jun. 3, 1997

[51] Int. Cl.$^6$ .................................. C07D 305/14
[52] U.S. Cl. ...................... 549/510; 549/414; 549/511
[58] Field of Search .......................... 549/510, 511, 549/414

[56] References Cited

FOREIGN PATENT DOCUMENTS

WO 94/18954  9/1994  WIPO .
WO 96/11683  4/1996  WIPO .

OTHER PUBLICATIONS

N. Palma, et al., Eur. Congr. Biotechnol., vol. 1, pp. 533–542, 1984, "Pleurmutilin Related Metabolites Produced By Submerged Culture Of The Basidiomycetous Genus Clitopilus Kummer".

Dreis B.A. De Bont, et al., Bioorganic & Medicinal Chemistry, vol. 5, No. 2, pp. 405–414, Feb. 1997, "Synthesis and Biological Activity of β-Glucuronyl Carbamate-Based Prodrugs Of Paclitaxel as Potential Candidates for Adept".

Koppaka V. Rao J. Heterocyclic Chem., vol. 34, No. 2, pp. 675–680, Mar. 1997, "Semi-Synthesis of Paclitaxel from Naturally Occurring Glycosidic Precursors".

Primary Examiner—Ba K. Trinh
Attorney, Agent, or Firm—Oblon, Spivak, McClelland, Maier & Neustadt, P.C.

[57] ABSTRACT

A taxoid derivative wherein sugar is combined with any one of paclitaxel, docetaxel and 10-deacetyl-bacatin III via a spacer. A method of producing the taxoid derivative comprises protecting hydroxyl groups at specific position of paclitaxel or docetaxel by protective compound followed by reacting with tetrabenzyl acetyloxyglucoside, and then carrying out debenzyl and detriethylsilyl reactions. A method of producing the taxoid derivative comprises reacting paclitaxel or docetaxel with tetrabenzyl acetyloxyglucoside, and then carrying out debenzyl reaction.

21 Claims, No Drawings

TAXOID DERIVATIVE AND METHOD OF PRODUCING THEREOF

FIELD OF THE INVENTION

The present invention relates to a taxoid derivative and method of producing it and, in detail, a taxoid derivative of which physiological activity and solubility in water were improved by combining sugar with any one of paclitaxel, docetaxel and 10-deacetyl-baccatin III via a spacer, and a method of producing the said derivative.

BACKGROUND OF THE INVENTION

Paclitaxel (trade name, Taxol) is a diterpene compound [M. C. Wani et al.: J. Am. Chem. Soc., 93, 2325 (1971)] isolated from bark of *Taxus brevifolia* growing in North America and known as a powerful anticancer drug having an improving effect on a uncurable cancer by a hitherto known chemical therapy. Mechanism of controling cancer with paclitaxel is unique and, while other anticancer drugs control formation of microtubule which is a main component of spindle, that is a mitosis device, paclitaxel causes excess formation of microtubule and thereby, controls mitosis.

Although paclitaxel is a powerful anticancer drug, its solubility in water is low, and its utility as a medical drug is limited. Because of this, use of a solubilizing agent and study and development, etc. to enhance its solubility by preparing derivatives are actively carried out, and any sufficient measure to solve this matter is not yet found. For example, paclitaxel is at present administered to a patient using a solubilizing agent "Cremophore", and 1 liter of the solution is administered for 6 hours every two weeks, a four-run of which is carried out, thus being a heavy burden on patients [Eric K. Rowinsky et al., CANCER RESEARCH 49, 4640 (1989)] and also, side effects of the solubilizing agent becomes a problem.

Further, although docetaxel (trade name: Taxotere) was developed as a paclitaxel derivative being improved in solubility, solubility of docetaxel in water is only 1.3 times that of paclitaxel [I. Ringer et al., J. Natl. Cancer Inst., 83, 288 (1991)], therefore it is not much improved.

To improve solubility of paclitaxel, introduction of various functional groups into a side chain and taxane ring was carried out and some compounds among prepared compounds showed improvement in solubility. However, the compound showing an increased physiological activity is not yet reported.

There is no report concerning a sugar derivative of paclitaxel and only a report describes that a compound comprising xylose by an ether linkage exists in Nature [H. Lataste et al., Proc. Natl. Acad. Sci. USA, 81, 4090 (1984)].

For chemical glucosylation there are many methods, for example, as described in Chapter 3 in Series of Experimental Chemistry, 4th Edition, Volume 26, (Organic Synthesis VIII), edited by The Chemical Society of Japan. In all cases, use of a heavy metal salt or strong Lewis acid is necessary. However, since paclitaxel and docetaxel have an oxetane skeleton being unstable for acid and a fundamental skeleton having large steric hinderance, a hitherto-known chemical glycosylation does not proceed effectively. On the other hand, enzymatic glycosylation does not produce an aimed compound because of very low solubility in water by paclitaxel and docetaxel.

Further, 10-deacetyl-baccatin III extracted from bark of *Taxus brevifolia* growing in North America, which is similar to paclitaxel, is a precursor of docetaxel. It is expected to develop a method of producing a hydrophilic taxoid derivative using this substance.

SUMMARY OF THE INVENTION

Under these circumstances, it is an object of the present invention to develop a sugar derivative of paclitaxel etc. showing an elevation in both solubility and physiological activity and thereby, to reduce a load of patients and provide an effective cancer treatment drug.

The present inventors carried out intensive investigation in order to develop paclitaxel derivatives and, as a result, have found that a paclitaxel derivative, in which sugar is combined with paclitaxel by an ether linkage via a spacer, is obtained and the derivative shows elevation of solubility in water and physiological activity, and thus the present invention was completed. Also, as to the aforementioned docetaxel and 10-deacetyl-baccatin III, a method to obtain taxoid derivatives in which sugar is similarly combined by an ether linkage was established.

The present invention relates to taxoid derivatives wherein sugar is combined with any one of paclitaxel, docetaxel and 10-deacetyl-baccatin III via a spacer and to a method for producing the said derivatives.

DETAILED DESCRIPTION OF THE PREFERRED EMBODIMENTS

Hereinafter, practical examples of taxoid derivatives of the present invention are shown below.

Glucosyloxyacetyl-7-paclitaxel represented by the following formula (hereinafter, abbreviated to 7-S-paclitaxel),

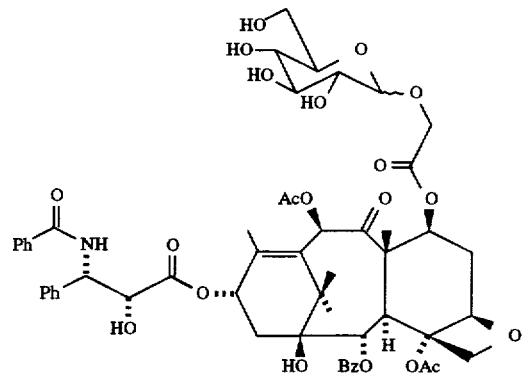

Glucosyloxyacetyl-2'-paclitaxel represented by the following formula (hereinafter, abbreviated as 2'-S-paclitaxel),

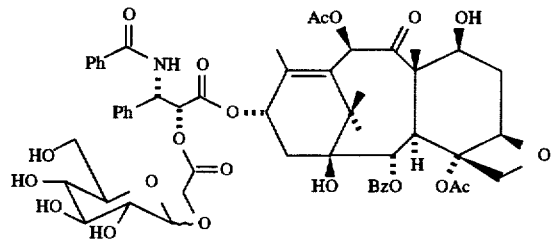

Diglucosyloxyacetyl-2',7-paclitaxel represented by the following formula (hereinafter, abbreviated to 2',7-S-paclitaxel),

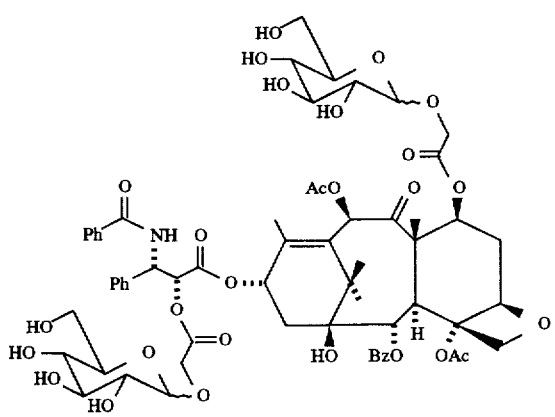

Glucosyloxyacetyl-10-paclitaxel represented by the following formula (hereinafter, abbreviated to 10-S-paclitaxel).

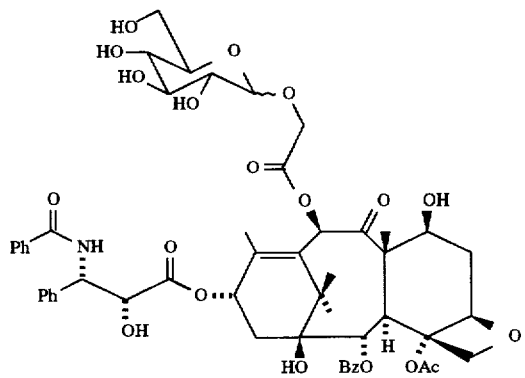

N-(glucosyloxyacetyl)-N-debenzoylpaclitaxel represented by the following formula (hereinafter, abbreviated to 3'-S-paclitaxel).

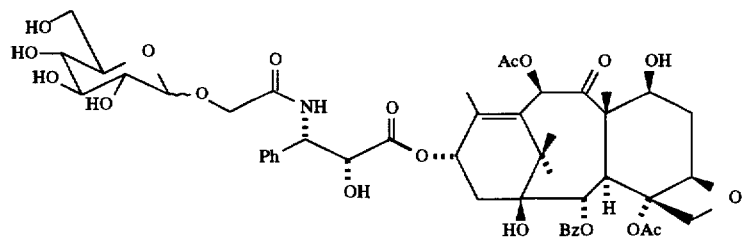

N-(glucosyloxyacetyl)-N-debutoxycarbonyldocetaxel represented by the following formula (hereinafter, abbreviated as 3'-S-docetaxel).

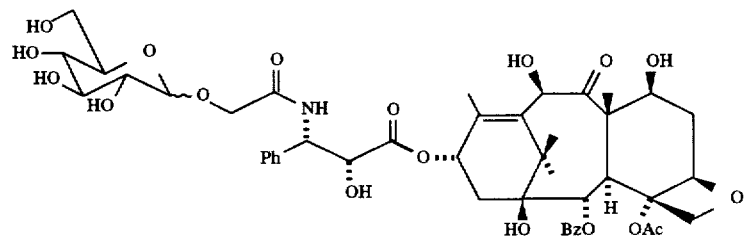

Glucosyloxyacetyl-2'-docetaxel represented by the following formula (hereinafter, abbreviated as 2'-S-docetaxel),

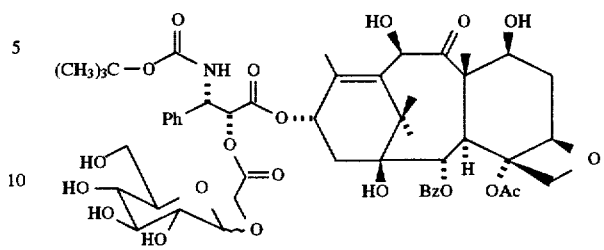

Diglucosyloxyacetyl-2',7-docetaxel represented by the following formula (hereinafter, abbreviated as 2',7-S-docetaxel),

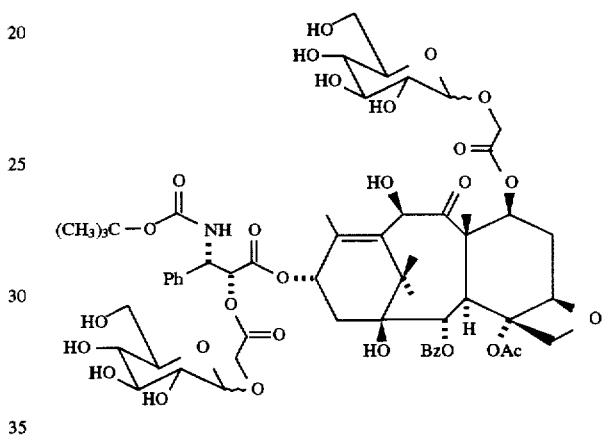

Triglucosyloxyacetyl-2',7,10-docetaxel represented by the following formula (hereinafter, abbreviated as 2',7,10-S-docetaxel),

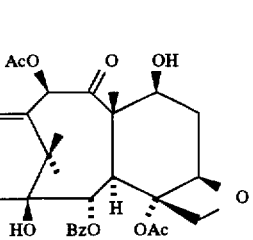

Glucosyloxyacetyl-7-docetaxel represented by the following formula (hereinafter, abbreviated as 7-S-docetaxel),

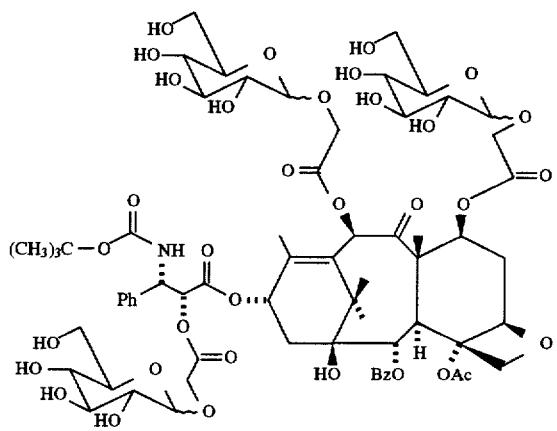

Diglucosyloxyacetyl-7,10-docetaxel represented by the following formula (hereinafter, abbreviated as 7,10-S-docetaxel),

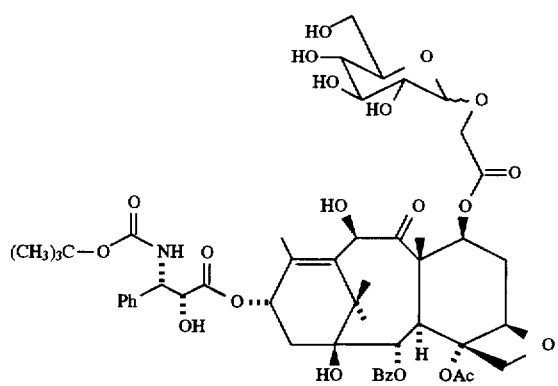

Glucosyloxyacetyl-10-docetaxel represented by the following formula (hereinafter, abbreviated as 10-S-docetaxel), Glucosyloxyacetyl-10-baccatin III represented by the following formula (hereinafter, abbreviated as 10-S-baccatin III).

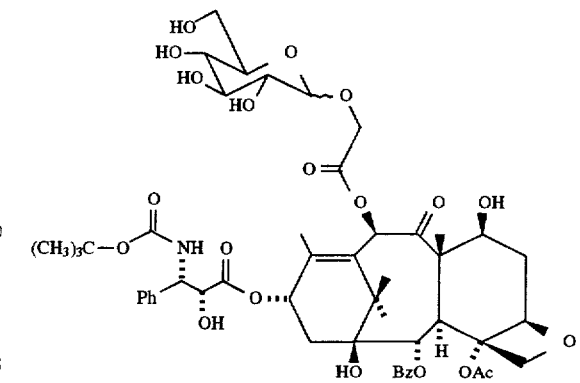

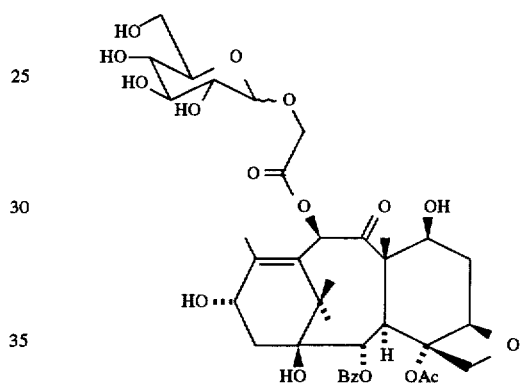

Hereinafter, the present invention is illustrated in detail. As described above, a taxoid derivative of this invention is made by combining sugar with any one of paclitaxel, docetaxel and 10-deacetyl-baccatin III via a spacer.

Paclitaxel is obtained by isolating from bark of *Taxus brevifolia* growing in North America according to a method described in Kingston, D. G. I.: Pharmacol. Ther., 52, 1 (1992)and, in addition, one synthesized by chemical synthesis is also used (R. A. Holton: Europian Patent-A 400971, 1990). Also, docetaxel is derived from paclitaxel according to a method described in Greene, A. E. et al.: J. Org. Chem. 59, 1238 (1994). 10-Deacetyl-baccatin III is a natural product extracted from *Taxus brevifolia* growing in North America as aforementioned.

A reaction combining sugar with any one of paclitaxel, docetaxel and 10-deacetyl-baccatin III via a spacer is carried out by using tetrabenzyl acetyloxyglucoside. This tetrabenzyl acetyloxyglucoside, an ester compound, is prepared by combining a glycolate such as ethyl glycolate etc., that is a spacer, with tetrabenzylglucose obtained by using glucose as a starting substance according to an usual procedure, and then deethylation of the ester gives tetrabenzyl acetyloxyglucoside as a carboxylic acid compound which is represented by the following formula.

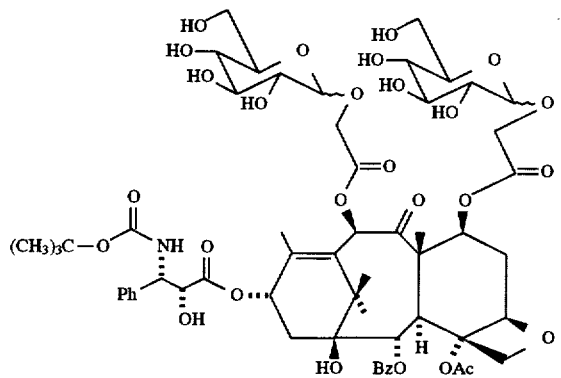

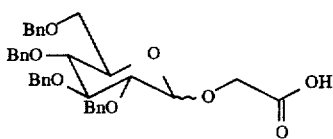

Next, one example of methods for producing tetrabenzyl acetyloxyglucoside is shown below.

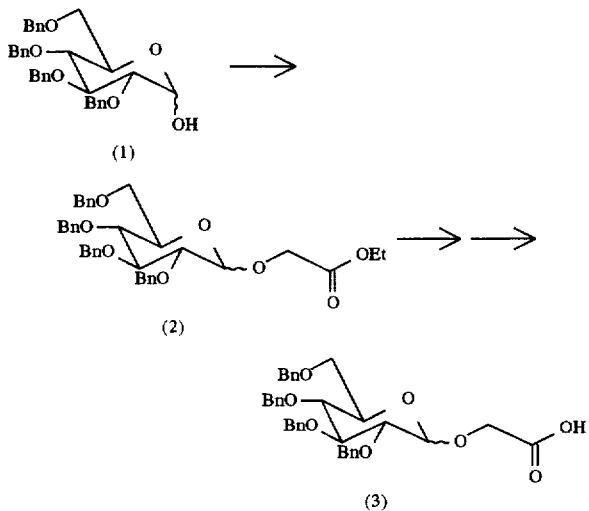

An ethyl ester (compound (2), molecular weight 626.76) is obtained by the method that tetrabenzylglucose (1) obtained according to an usual procedure is treated with ethyl glycolate and p-toluenesulfonic acid in benzene at 0°–150° C., preferably 110° C., for 0.5–50 hours, preferably 8 hours, so that the 1 position of tetrabenzylglucose (1) reacts with ethyl glycolate. Then, after treating the ethyl ester (2) in an alkali (for example, 6N-NaOH) in methanol-dioxane solution at from room temparature to 100° C. for 0.5–50 hours, preferably 3 hours, this reaction mixture is changed to an acidic condition by hydrochloric acid (for example, 1N-HCl) to cause a deethylation reaction, whereby a carboxylic acid compound is obtained which is tetrabenzyl acetyloxyglucoside (3). Further, in the case of using other sugar instead of glucose, corresponding sugar-modificated compounds whose sugar is different can be obtained according to a similar reaction. As the kind of sugar using in this case, for example, there are mannose, allose, altose, gulose, idose, galactose, talose, ribose, arabinose, xylose, lyxose, psicose, fructose, sorbose, tagatose, fucose, maltose and so forth in addition to glucose.

In this invention, although a glycolate such as ethyl glycolate is used as a spacer of a sugar donor, by changing the alkyl chain length of this substance, length of the spacer can be easily adjusted. For example, it is possible to use 3-hydroxybutyric acid and so forth as a spacer.

A taxoid derivative of this invention can be produced by allowing any one of the aforementioned paclitaxel, docetaxel and 10-deacetyl-baccatin III to react with tetrabenzyl acetyloxyglucoside. As practical examples of methods for producing taxoid derivatives, there are methods shown in the below-described reaction processes (I) and (II).

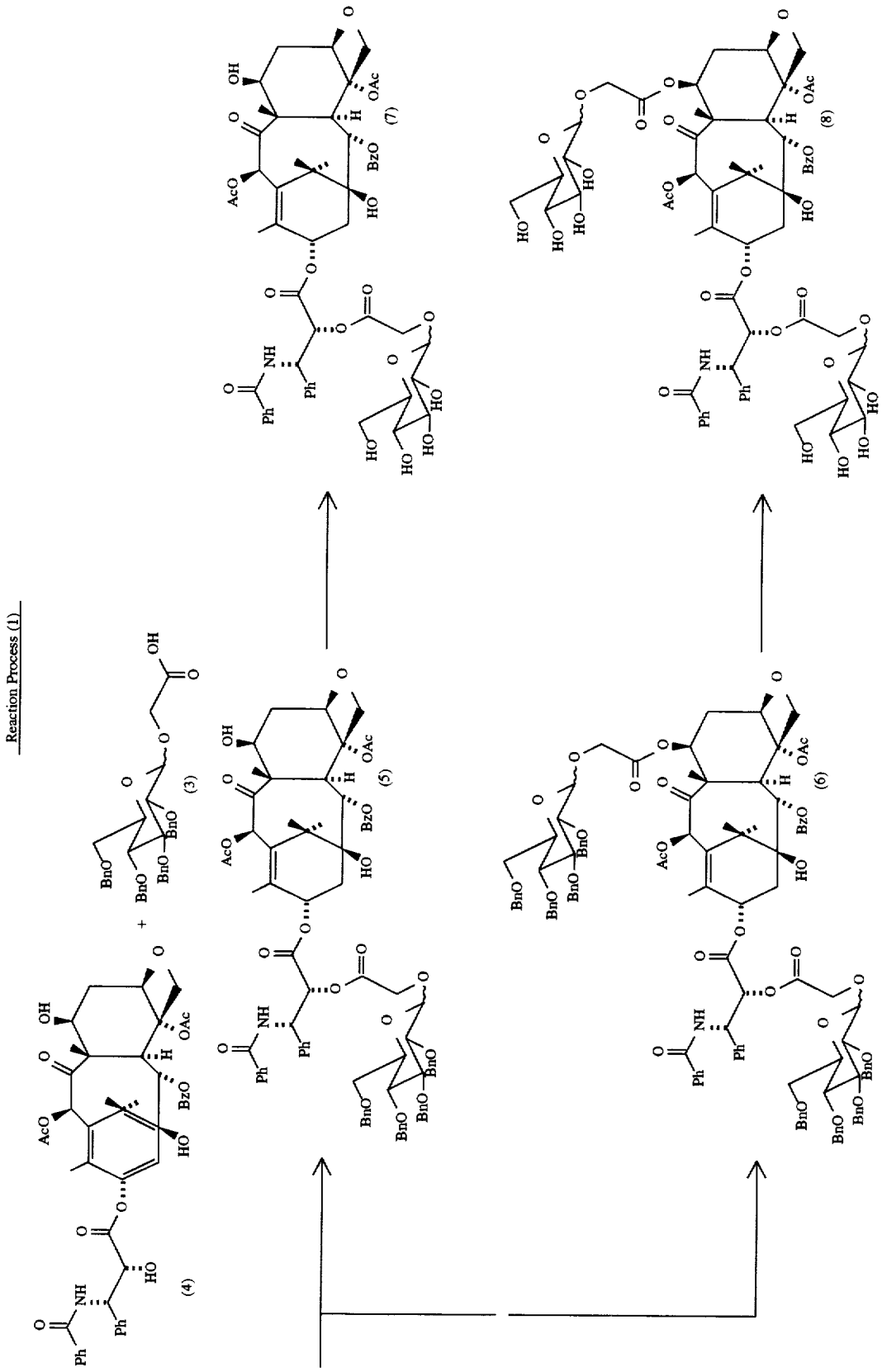

Reaction Process (II)
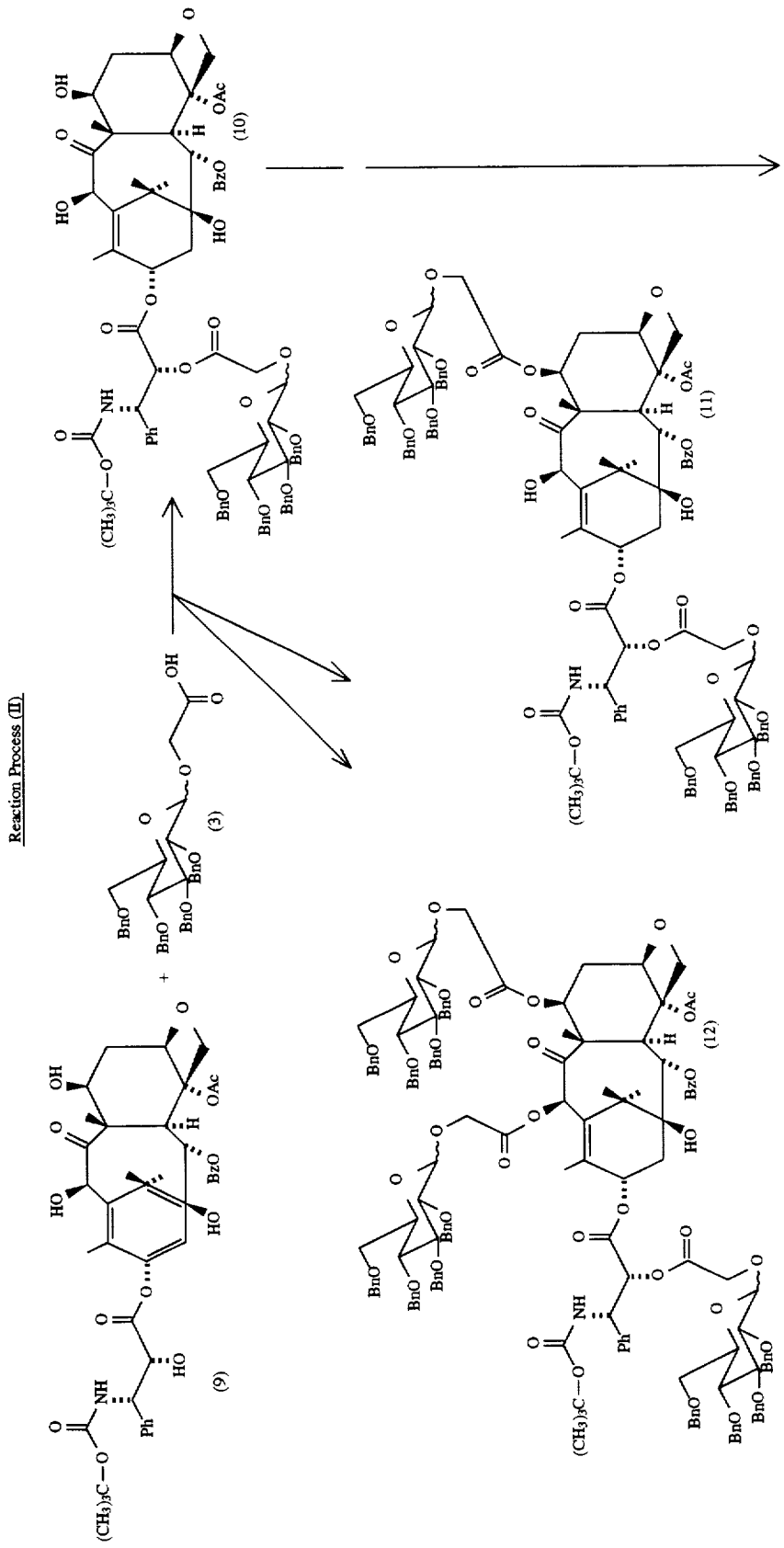

-continued
Reaction Process (II)
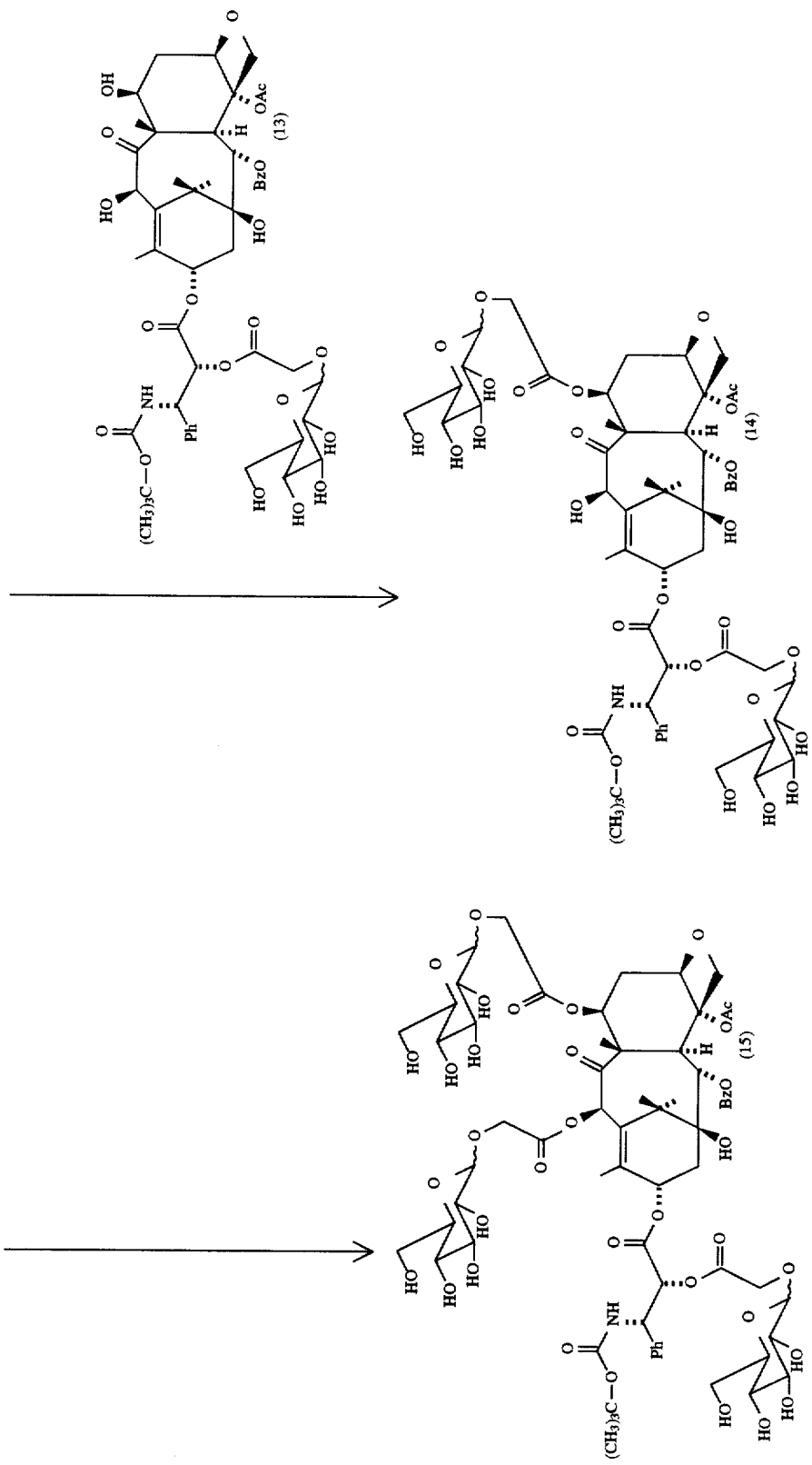

The method shown in the reaction process (I) is such that debenzylation is carried out after allowing paclitaxel (4) to react with tetrabenzyl acetyloxyglucoside (3) and, according to this method, 2'-S-paclitaxel (7) and 2',7-S-paclitaxel (8) are obtained.

That is, paclitaxel (4) and tetrabenzyl acetyloxyglucoside (3) are allowed to react with a base such as 4-dimethylaminopyridine (DMAP) etc., a condensing reagent such as dicyclohexylcarbodiimide (DCC) etc. and a solvent such as methylene chloride etc. under an argon atmosphere at room temperature for 0.5–100 hours, preferably 16.5 hours, whereby the glucoside (5) or (6) is obtained.

Next, in order to carry out debenzylation the compound (5) or (6) is allowed to react with a catalyst such as palladium black etc. and an acid such as acetic acid etc. under a hydrogen atmosphere at room temperature with vigorous stirring for 0.5–50 hours, preferably 5 hours, whereby 2'-S-paclitaxel (7) and 2',7-S-paclitaxel (8) are obtained.

Further, in the case of using docetaxel (9) instead of paclitaxel, according to the reaction process (II), 2'-S-docetaxel (13), 2',7-S-docetaxel (14) and 2',7,10-S-docetaxel (15) represented by the above can be obtained via the glucoside (10), (11) or (12).

Also, the method (III) shown by the below-described reaction process is such that, after protecting the 2'-position of paclitaxel by using a chlorotriethylsilyl group, a reaction with tetrabenzyl acetyloxyglucoside followed by debenzylation and detriethylsilylation are carried out to produce a paclitaxel derivative.

Reaction Process (III)

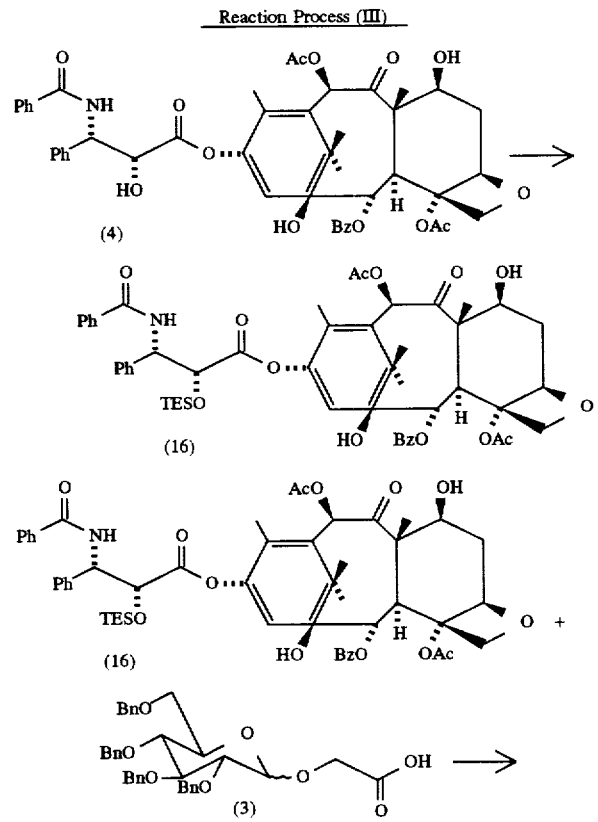

Reaction Process (III) —continued

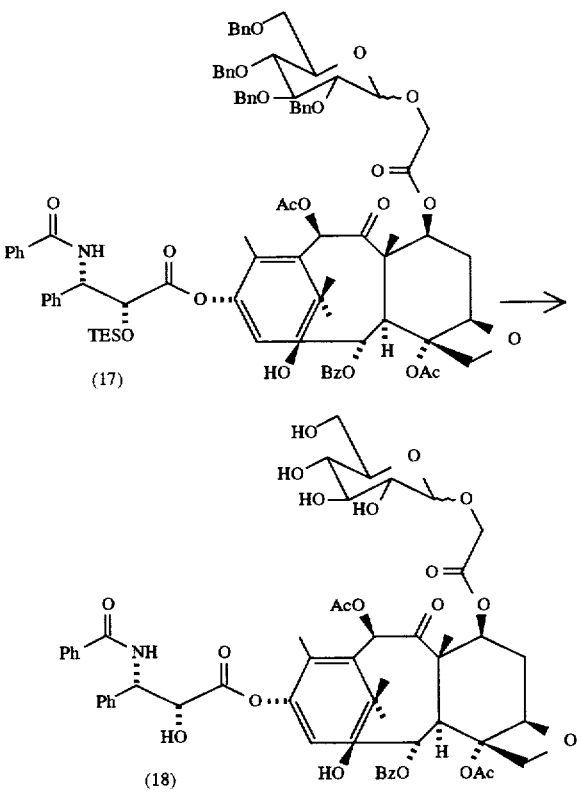

At first, paclitaxel (4) with a protecting reagent such as chlorotriethylsilane (TESCl) etc., a base such as imidazole etc. and a solvent such as dimethylformamide (DMF) etc. is allowed to react under an argon atmosphere at room temperature for 0.5–100 hours, preferably 19.5 hours, whereby the 2' position of paclitaxel is protected by triethylsilane and the compound (16) is obtained.

Next, this obtained compound with tetrabenzyl acetyloxyglucoside (3), a base such as DMAP etc., a condensing reagent such as DCC etc. and a solvent such as methylene chloride etc. is allowed to react under an argon atmosphere at room temperature for 0.5–100 hours, preferably 5 hours, whereby the glycoside (17) is obtained.

Next, the glycoside (17) with a catalyst such as palladium black etc. and an acid such as acetic acid etc. is allowed to react under a hydrogen atmosphere at room temperature with vigorous stirring for 0.5–50 hours, prefrably 5 hours, and to this reaction mixture a solvent such as tetrahydrofuran (THF) etc. and water are added to carry out a reaction at room temperature for 0.5–50 hours, prefrably 15 hours, whereby an aimed compound (18) is obtained which is 7-S-paclitaxel represented by the above formula.

Further, by using docetaxel (9) instead of paclitaxel, 7-S-docetaxel (19), 7,10-S-docetaxel (20) and 10-S-docetaxel (21) represented by the below-described formulae can be obtained.

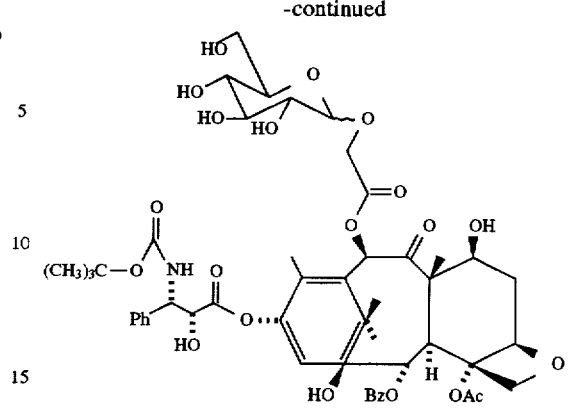

(19)

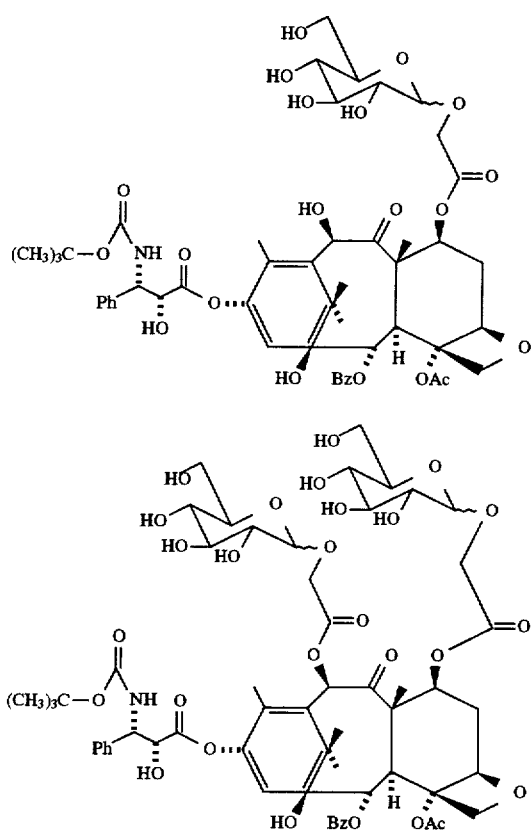

(20)

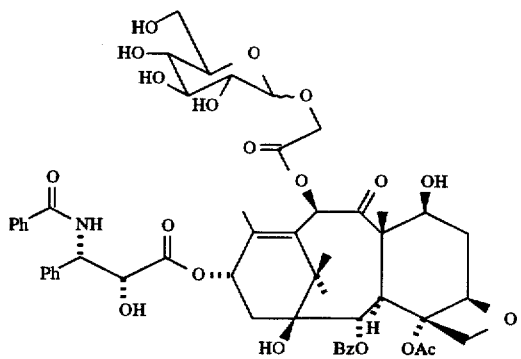

(21)

Also, by using 10-deacetylpaclitaxel (22) instead of paclitaxel, 10-S-paclitaxel (23) represented by the below-described formula can be obtained. By using N-debenzoylpaclitaxel (24) instead of paclitaxel, 3'-S-paclitaxel (25) represented by the below-described formula can be obtained. Similar to the above, 3'-S-docetaxel (38) can be obtained. Further, by using 10-deacetyl-baccatin III (26) instead of paclitaxel, 10-S-baccatin III (27) represented by the below-described formula can be obtained.

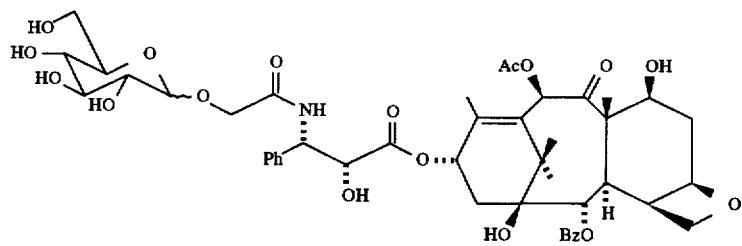

(23)

(25)

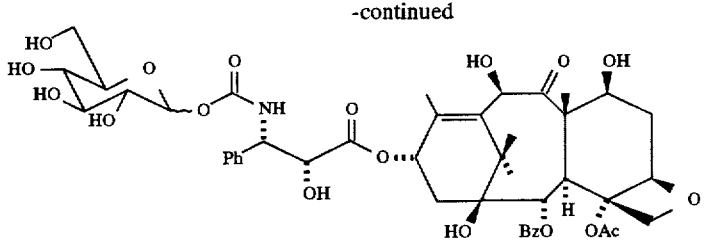

(38)

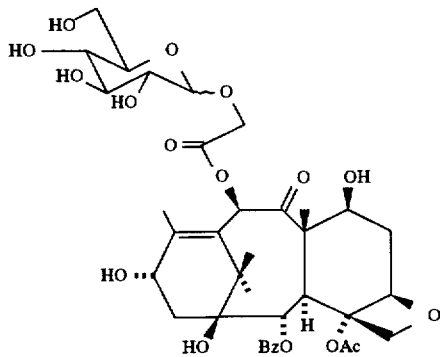

(27)

Taxoid derivatives of this invention are able to separate easily an anomer by applying a liquid chromatography which uses a carrier having silica gel such as ODS etc. and thus, a purified sample is obtained which can be used as a medicine.

These taxoid derivatives all show increased solubility in water and, while the solubility of paclitaxel is 0.4 μg/ml, that of 7-S-paclitaxel is 14.7 μg/ml (36.8 times), 2'-S-paclitaxel 30.6 μg/ml (76.5 times) and 2',7-S-paclitaxel 48.4 μg/ml (121 times). These paclitaxel derivatives also show increased solubility in alcohol.

Also, when physiological activity of these paclitaxel derivatives is relatively evaluated taking activity for inhibiting depolymerization of microtubule as 100, 7-S-paclitaxel is 225, 2'-S-paclitaxel 100 and 2',7-S-paclitaxel 77.7. Therefore, physiological activity of each paclitaxel derivative is sufficiently maintained and it is possible to use taxoid derivatives of this invention as an anticancer drug. When galactose or mannose is used as sugar, because they have affinity with hepatocyte, derivatives effective on medical treatment of liver cancer are obtained.

The present invention provides a taxoid derivative which shows a high solubility in water and improved physiological activity and a method for producing it. It is expected that the taxoid derivative reduces a burden on patients and is used as an effective drug for the treatment of cancer.

EXAMPLE

The present invention will be illustrated in more detail by means of the following examples.

Production Example 1

A mixture of 1.62 g of tetrabenzylglucose (1) obtained by the conventional method, 1.56 g of ethyl glycolate, 0.10 g of p-toluenesulfonic acid and 80 ml of benzene was allowed to react under reflux at 110° C. for 8 hours, whereby the compound (2) ($C_{38}H_{42}O_8$, molecular weight 626.74) was obtained.

Next, 1.88 g of this compound was allowed to react with 10 ml of 6N-NaOH, 10 ml of methanol and 15 ml of dioxane at from room temperature to 100° C. for 3 hours. This mixture was transferred into 80 ml of 1N-HCl to carry out deethylation, whereby the compound (3) that is a carboxylic acid compound ($C_{38}H_{38}O_8$, molecular weight 598.69) was obtained.

The compound (3) was dissolved into deuteriumchloroform and analyzed by $^1$H-NMR, and each peak was assigned to determine its structure and thus, structure of the compound was confirmed as the above-described.

Example 1

A mixture of 256 mg of paclitaxel (4) ($C_{47}H_{51}NO_{14}$, molecular weight 853.92), 539 mg of tetrabenzyl acetyloxyglucoside (3) obtained from Production Example 1, 110 mg of 4-dimethylaminopyridine. (DMAP), 186 mg of dicyclohexylcarbodiimide (DCC) and 8 ml of methylene chloride was allowed to react under an argon atmosphere at room temperature for 16.5 hours, whereby a compound converted into a glucoside at the 2' position (5) ($C_{83}H_{87}NO_{21}$, molecular weight 1434.59) and a compound converted into a glucoside at the 2',7 positions (6) ($C_{119}H_{123}NO_{28}$, molecular weight 2015.27) were obtained.

Debenzylation of 187 mg of the compound (5) was carried out by reacting with 50 mg of palladium black and 3 ml of acetic acid under a hydrogen atmosphere at room temperature with a vigorous stirring for 5 hours, whereby 101 mg of 2'-S-paclitaxel (7) ($C_{55}H_{83}NO_{21}$, molecular weight 1074.10) were obtained. The yield was 73%. Also, debenzylation of 983 mg of the compound (6) was carried out by reacting with 200 mg of palladium black and 3 ml of acetic acid under a hydrogen atmosphere at room temperature with a vigorous stirring for 5 hours, whereby 259 mg of 2',7-S-paclitaxel (8) ($C_{63}H_{75}NO_{28}$, molecular weight 1294.28) were obtained. The yield was 41%.

Next, using a column (φ20 mm, volume 40 ml) filled by silica gel (trade name: Kieselguhr, made by Merck Co., Ltd.) and chloroform as a mobile phase, 2'-S-paclitaxel and 2',7-S-paclitaxel were separately purified.

Example 2

A mixture of 427 mg of paclitaxel (4), 0.1 mg of chlorotriethylsilane (TESCl), 102 mg of imidazole and 5 ml of DMF was allowed to react under an argon atmosphere at room temperature for 19.5 hours, whereby a compound protected by a triethylsilyl group at the 2' position of paclitaxel (16) ($C_{53}H_{65}NO_{14}Si$, molecular weight 968.18) was obtained. A mixture of 392 mg of this compound (16), 479 mg of tetrabenzyl acetyloxyglucoside (3), 98 mg of DMAP, 165 mg of DCC and 8 ml of methylene chloride was allowed to react under an argon atmosphere at room temperature for 5 hours, whereby the glucoside (17) ($C_{89}H_{101}NO_{21}Si$, molecular weight 1548.86) was obtained.

Next, 513 mg of the obtained compound (17) with 100 mg of palladium black and 3 ml of acetic acid were allowed to react under a hydrogen atmosphere at room temperature with a vigorous stirring for 5 hours and further, 1 ml of tetrahydrofuran (THF) and 1 ml of water were added to the reaction mixture, which was then allowed to react at room temperature for 15 hours to obtain 350 mg of 7-S-paclitaxel (18) ($C_{55}N_{63}NO_{21}$, molecular weight 1074.10).

Next, using a column (φ20 mm×250 mm) filled by silica gel (trade name: ODS, made by YMC Co., Ltd.) and methanol as a mobile phase, each anomer of 7-S-paclitaxel was purified.

7-S-paclitaxel was dissolved into deuteriumchloroform and analysed by $^1$H-NMR and the structure was determined by assigning respective peaks. Results are shown below.

$^1$H-NMR of 7-S-paclitaxel (α-anomer) (500 MHz, $CDCl_3$) 1.12 (s, 3H, $CH_3$), 1.18 (s, 3H, $CH_3$), 1.77 (s, 3H, $CH_3$), 1.83 (s, 3H, $CH_3$), 2.15 (s, 3H, $CH_3$), 2.35 (s, 3H, $CH_3$), 1.6–2.55 (m, 5H), 3.4–3.9 (m, 7H), 4.0–4.4 (m, 4H), 4.75–5.1 (m, 3H), 5.5–5.8 (m, 3H), 6.05–6.2 (m, 1H), 7.2–7.6 (m, 11H, Ar, NH), 7.6–7.7 (m, 1H, Ar), 7.7–7.9 (m, 2H, Ar), 8.1–8.2 (m, 2H, Ar)

$^1$H-NMR of 7-S-paclitaxel (β-anomer) (500 MHz, $CDCl_3$) 1.14 (s, 3H, 17-$CH_3$), 1.20 (s, 3H, $CH_3$), 1.81 (s, 3H, $CH_3$), 1.84 (s, 3H, $CH_3$), 2.17 (s, 3H, $CH_3CO$), 2.38 (s, 3H, $CH_3CO$), 2.25–2.35 (m, 2H), 2.5–2.7 (m, 2H), 3.3–3.9 (m, 5H), 4.1–4.5 (m, 4H), 4.85 (br, 1H, H2'), 4.95 (brd, J=9.1, 1H, H5), 5.5–5.8 (m, 3H), 6.1–6.2 (m, 2H), 7.3–7.6 (m, 11H, Ar, NH), 7.6–7.7 (m, 1H, Ar), 7.7–7.8 (m, 2H, Ar), 8.1–8.2 (m, 2H, Ar)

Example 3

Ten milligram of paclitaxel, 7-S-paclitaxel, 2'-S-paclitaxel and 2',7-S-paclitaxel was separately weighted and 5 ml of water were added to each compound, which was stirred for 18 hours. After stirring, supernatant was filtered by a membrane filter (0.45 μm) and a filtate was analyzed by HPLC. As a result, solubility in water of each compound was as shown in Table 1. Further, analysis conditions were as described below.

Colum: Taxil 5μ (4.6×250 mm), made by MetaChem
Solvent: $MeOH/H_2O$ (80/20)
Flow rate: 0.5 ml/min
Detector: photodiode detector (230 nm)
Injected amount: 20 μl

TABLE 1

| Sample | Solubility (μg/ml) |
| --- | --- |
| Paclitaxel | 0.4 |
| 7-S-paclitaxel | 14.7 |
| 2'-S-paclitaxel | 30.6 |
| 2',7-S-paclitaxel | 48.4 |

As clearly shown in Table, compared with paclitaxel, the solubility of paclitaxel derivatives show strikingly high values. However, it was recognized that 2'-S-paclitaxel and 2',7-S-paclitaxel are decomposed to paclitaxel in aqueous solutions and unstable in aqueous solutions.

Example 4

Paclitaxel, 7-S-paclitaxel, 2'-S-paclitaxel and 2',7-S-paclitaxel were separately dissolved into dimethylsulfoxide (DMSO), and an inclusion complex (made by Ensuiko Sugar Refining Co., Ltd.) of dimethyl-β-cyclodextrin (DM-β-CD, made by Ensuiko Sugar Refining Co., Ltd.) with paclitaxel was dissolved in water so that the concentrations of these compounds in the reaction solutions were adjusted at 5 μM.

Next, each of the above-described samples is mixed with tubulin (a main constituting protein of microtubule) and allowed to react at 37° C. for 15 minutes. Absorbance at 350 nm of the reaction solution was measured at 2, 5, 10 and 15 minutes after initiation of the reaction. Also, after the reaction ended, calcium chloride was added and, 5 minutes after this adding, absorbance at 350 nm was again measured. From each measured value was determined relative activity of each sample in the case that polymerization-promoting activity and depolymerization-inhibiting activity were taken as 100, and the results are shown in Table 2.

As clearly shown in Table, depolymerization-inhibiting activity of 7-S-paclitaxel is more than twice as potent as that of paclitaxel and it was confirmed that 7-S-paclitaxel is a very effective anticancer drug. Also, it was recognized that the polymerization-promoting activity is enhanced by making a complex which includes paclitaxel in DM-β-CD.

TABLE 2

| Sample | Polymerization-promoting activity | Depolymerization-inhibiting activity |
| --- | --- | --- |
| Paclitaxel | 100 | 100 |
| 7-S-paclitaxel | 91.9 | 225 |
| 2'-S-paclitaxel | 52.7 | 100 |
| 2',7-S-paclitaxel | 40.5 | 77.7 |
| DM-β-CD-paclitaxel | 123 | 62.7 |

Example 5

Similar to Example 1, a mixture of 260 mg of docetaxel, 540 mg of tetrabenzyl acetyloxyglucoside obtained from Production Example 1, 110 mg of DMAP, 190 mg of DCC and 8 ml of methylene chloride was allowed to react under an argon atmosphere at room temperature for 16.5 hours, whereby the compound (10) converted into a glucoside at the 2' position, compound (11) converted into a glucoside at the 2',7 positions and compound (12) converted into a glucoside at the 2',7,10 positions were obtained.

Next, similar to Example 1, each glucoside underwent debenzylation to obtain 2'-S-docetaxel (13), 2',7-S-docetaxel (14) and 2',7,10-S-docetaxel (15), respectively. These compounds are produced by the aforementioned reaction process (II).

Example 6

Using docetaxel (9) instead of paclitaxel, in a similar manner to the above Example 2, the compound (28) in which the 2' position of docetaxel was protected by a triethylsilyl group (TES) was obtained and then, the compounds (29) and (30) were obtained by reacting the compound (28) with tetrabenzyl acetyloxyglucoside (3) obtained from Production Example 1. Then, benzyl groups and TES were removed from the compounds (29) and (30), whereby 7-S-docetaxel (19) and 7,10-S-docetaxel (20) were obtained. These are produced by the reaction process (IV).
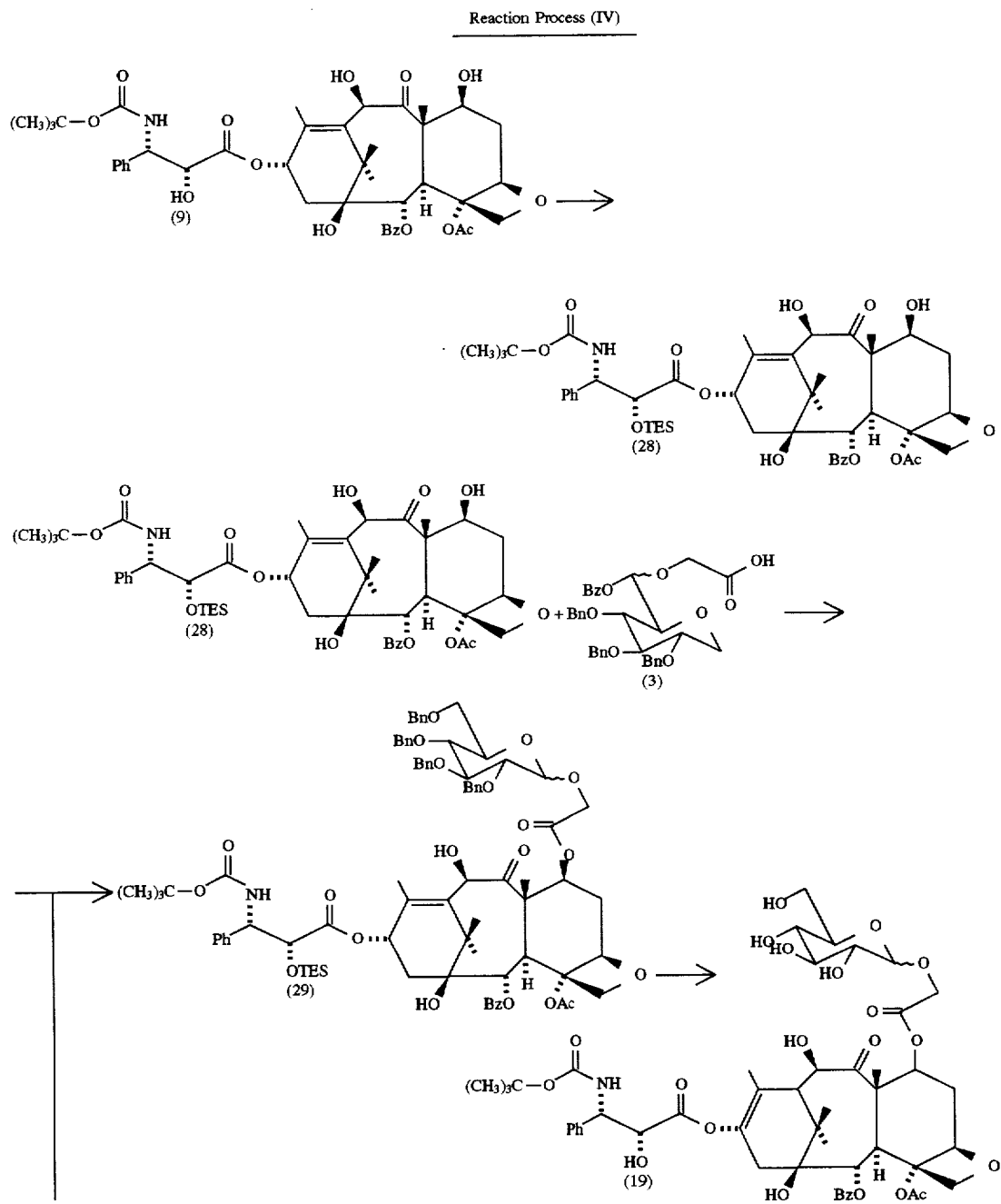

-continued
Reaction Process (IV)

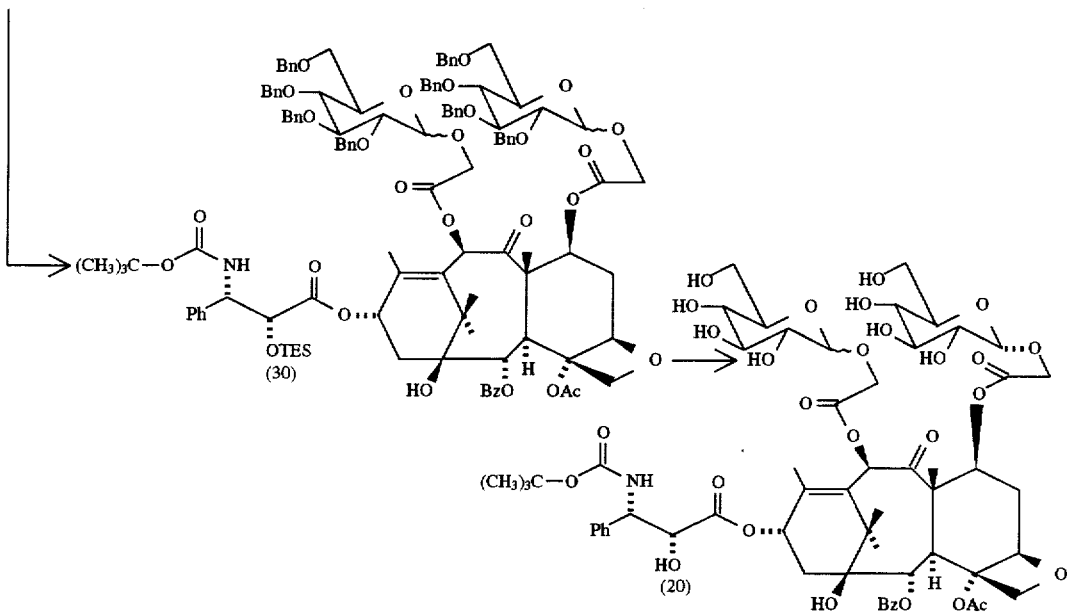

Example 7

Using docetaxel (9) instead of paclitaxel, in a similar manner to the above Example 2, the compound (31) in which the 2',7 positions of docetaxel were protected by TES was obtained and then, the compound (32) was obtained by reacting the compound (31) with tetrabenzyl acetyloxyglucoside (3) obtained from Production Example 1. Then, benzyl groups and TES were removed from the compound (32), whereby 10-S-docetaxel (21) ($C_{51}H_{65}NO_{21}$, molecular weight 1028.07) was obtained. This compound is produced by the reaction process (V).

Reaction Process (V)

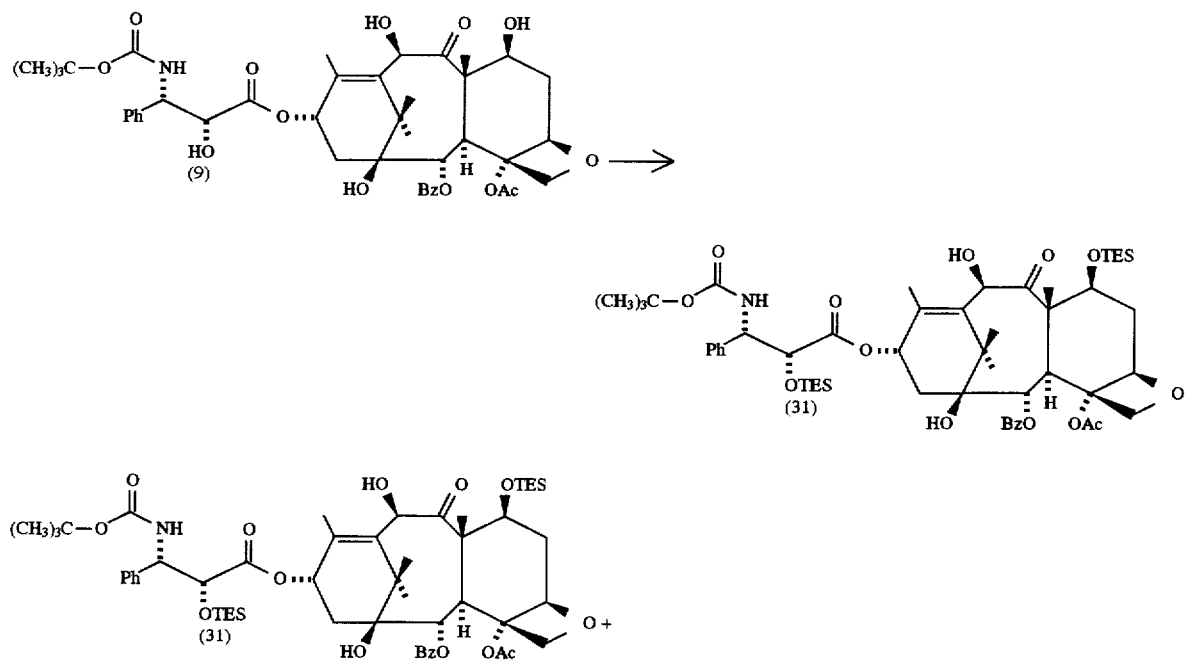

-continued
Reaction Process (V)

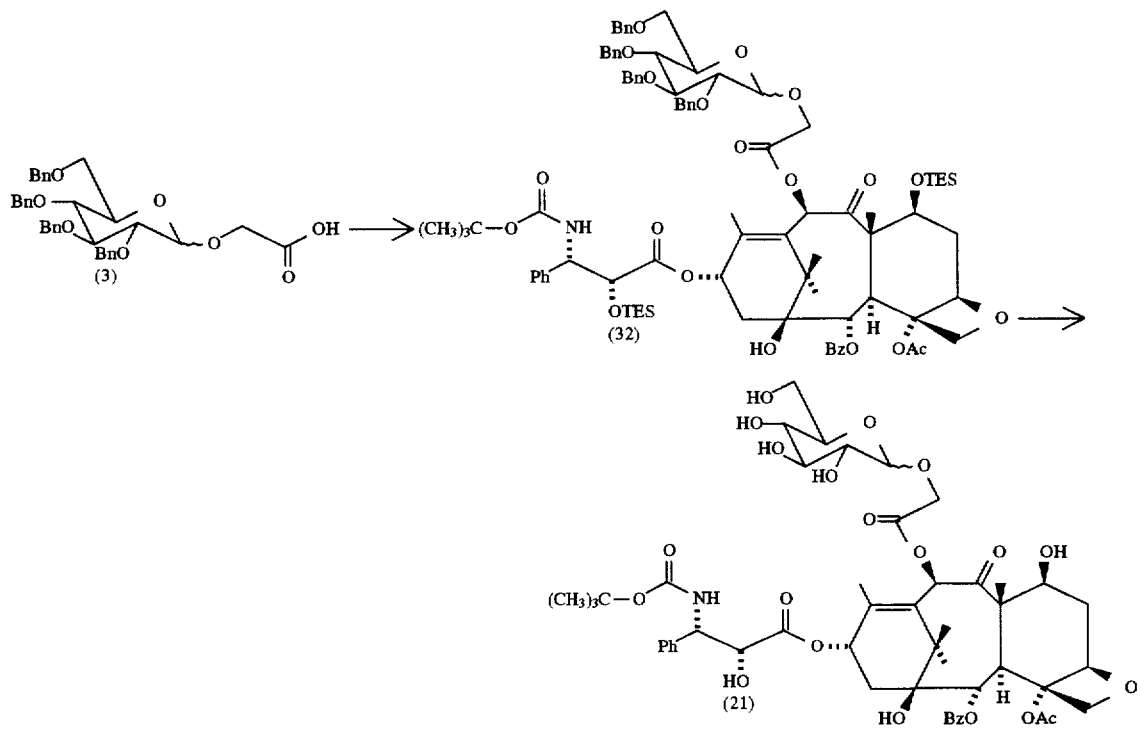

Example 8

Using 10-deacetylpaclitaxel ($C_{45}H_{49}NO_{13}$; molecular weight 811.88) (22) instead of paclitaxel, in a similar manner to the above Example 2, the compound (33) in which the 2',7 positions of 10-deacetylpaclitaxel were protected by TES was obtained and then, the compound (34) was obtained by reacting the compound (33) with tetrabenzyl acetyloxyglucoside (3) obtained from Production Example 1. Then, benzyl groups and TES were removed, whereby 10-S-paclitaxel ($C_{53}H_{61}NO_{20}$, molecular weight 1032.06) (23) was obtained. This compound is produced by the reaction process (VI).

Reaction Process (VI)

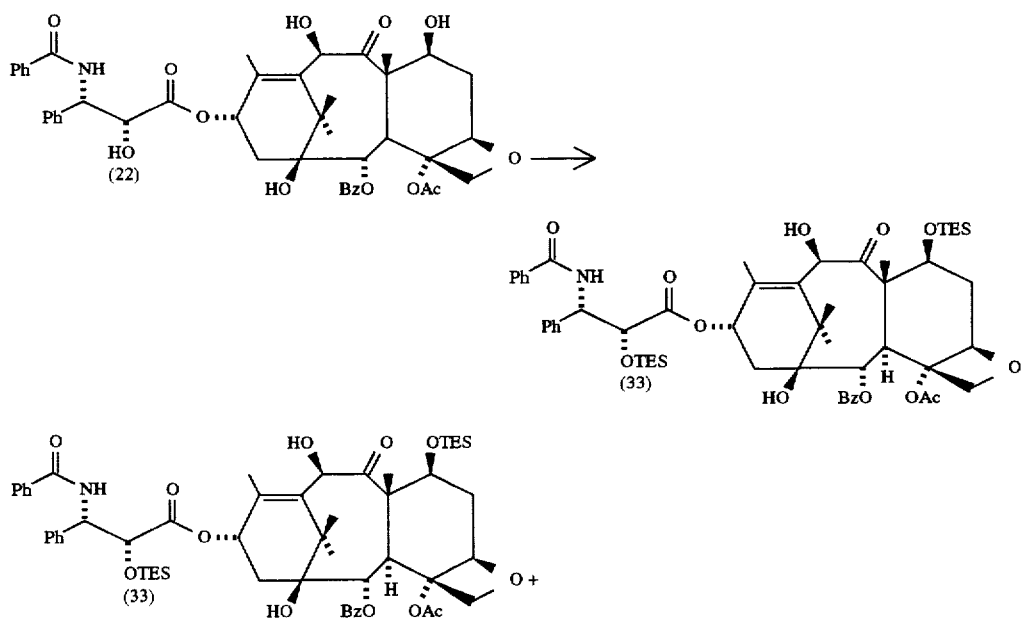

-continued
Reaction Process (VI)

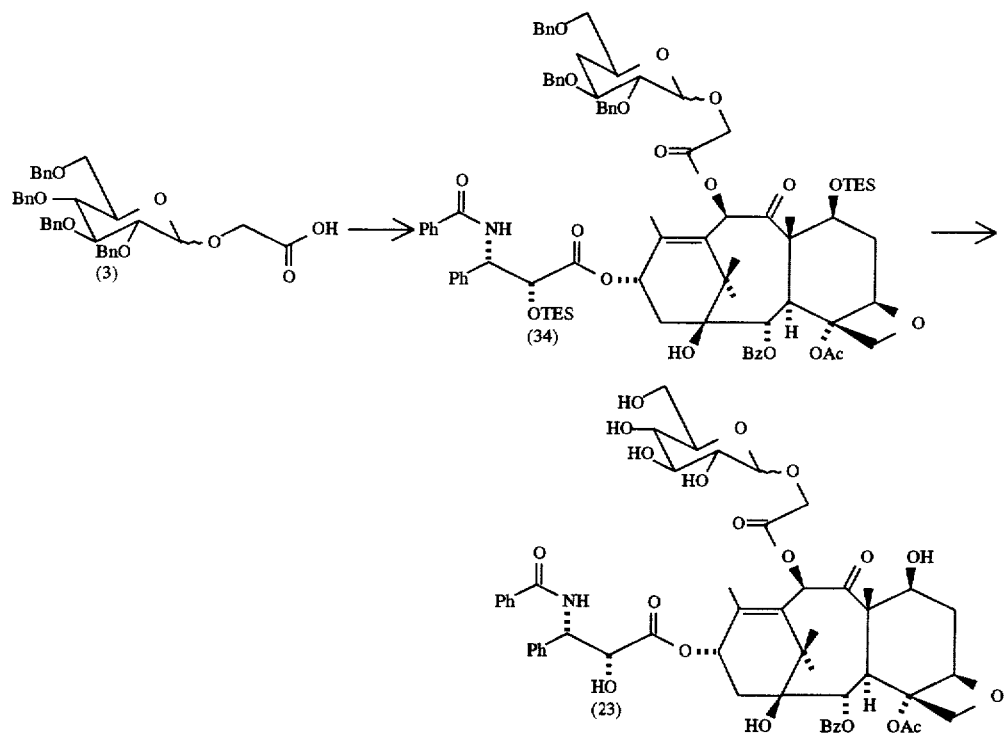

Example 9

Using N-debenzoylpaclitaxel ($C_{40}H_{47}NO_{13}$; molecular weight 749.81) (24) instead of paclitaxel, in a similar manner to the above Example 2, the compound (35) was obtained by reacting the compound with tetrabenzyl acetyloxyglucoside (3) obtained from Production Example 1. Then, benzyl groups were removed to obtain 3'-S-paclitaxel ($C_{48}H_{59}NO_{20}$, molecular weight 969.99) (25). This compound is produced by the reaction process (VII).

Also, using N-debutoxycarbonyldocetaxel as a starting material, in a similar manner to the above-described, it is possible to produce N-(glucosyloxyacetyl)-N-debutoxycarbonyldocetaxel which is a docetaxel type glucoside of 3'-S-paclitaxel.

Reaction Process (VII)

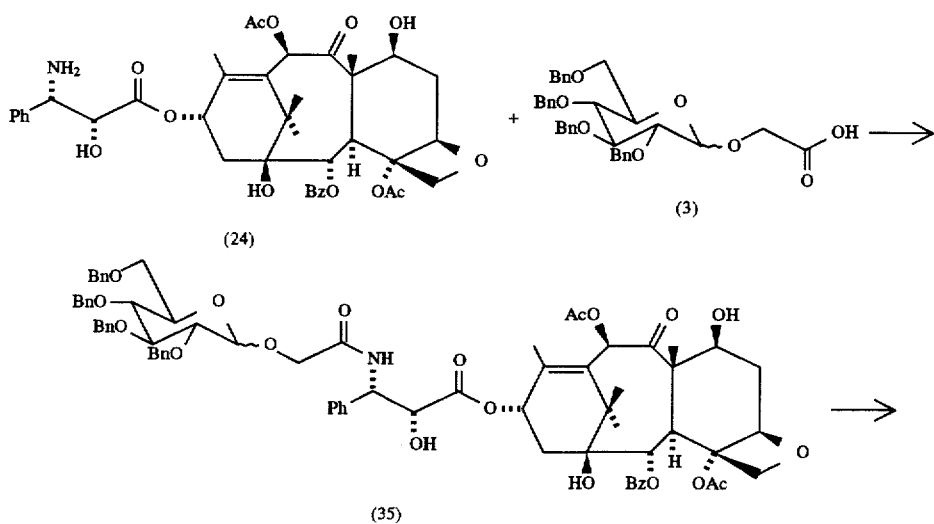

-continued
Reaction Process (VII)

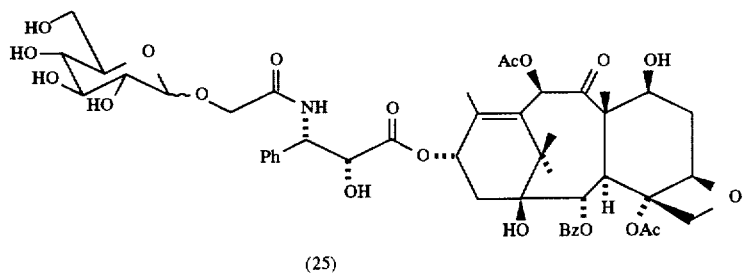

(25)

Example 10

Using 10-deacetyl-baccatin III ($C_{29}H_{36}O_{10}$; molecular weight 544.60) (26) instead of paclitaxel, in a similar manner to the above Example 2, the compound (36) in which the 7 position of 10-deacetylbaccatin III was protected by TES was obtained and then, the compound (37) was obtained by reacting the compound (36) with tetrabenzyl acetyloxyglucoside (3) obtained from Production Example 1. Then, benzyl groups and TES were removed to obtain 10-S-baccatin III ($C_{37}H_{48}O_{17}$; molecular weight 764.78) (27). This compound is produced by the reaction process (VIII) and effective as an intermediate compound to synthesize a hydrophilic taxoid.

-continued
Reaction Process (VIII)

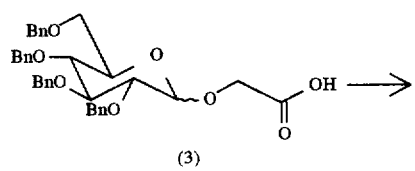

(3)

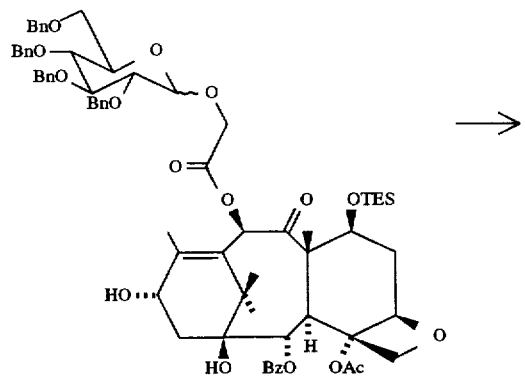

(37)

Reaction Process (VIII)

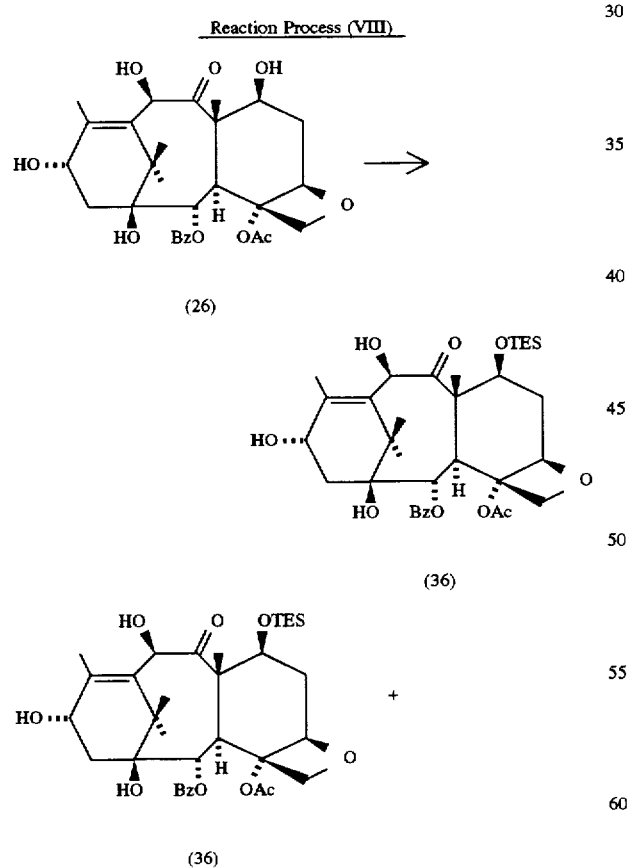

(26)

(36)

(36)

(27)

What is claimed is:

1. A taxoid derivative wherein sugar is combined with any one of paclitaxel, docetaxel and 10-deacetyl-baccatin III via a spacer.

2. The taxoid derivative according to claim 1, wherein the sugar is a sugar selected from the group consisting of glucose, mannose, allose, altrose, gulose, idose, galactose, talose, ribose, arabinose, xylose, lyxose, psicose, fructose, sorbose, tagatose, fucose and maltose.

3. The taxoid derivative according to claim 1, wherein the spacer is glycolate.

4. Glucosyloxyacetyl-7-paclitaxel represented by the following formula.

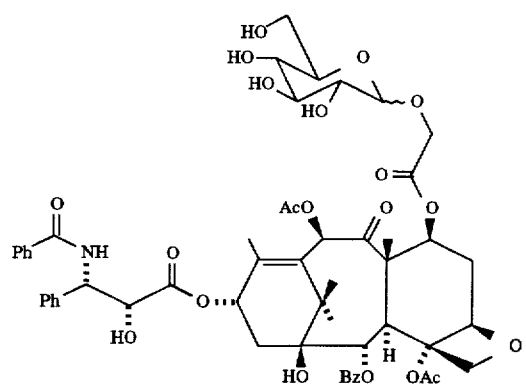

5. Glucosyloxyacetyl-2'-paclitaxel represented by the following formula.

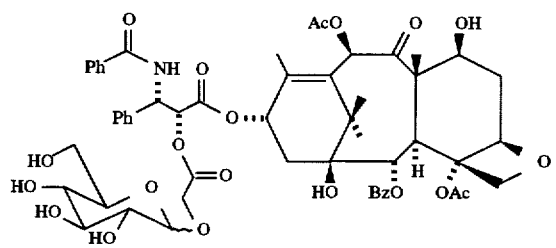

6. Diglucosyloxyacetyl-2',7-paclitaxel represented by the following formula.

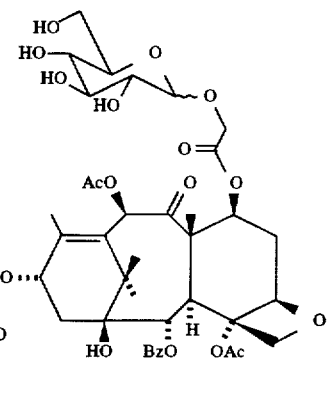

7. Glucosyloxyacetyl-10-paclitaxel represented by the following formula.

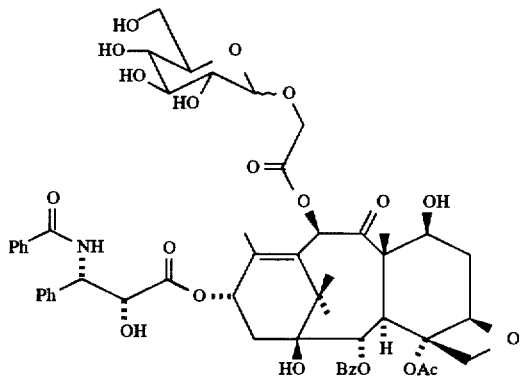

8. N-(glucosyloxyacetyl)-N-debenzoylpaclitaxel represented by the following formula.

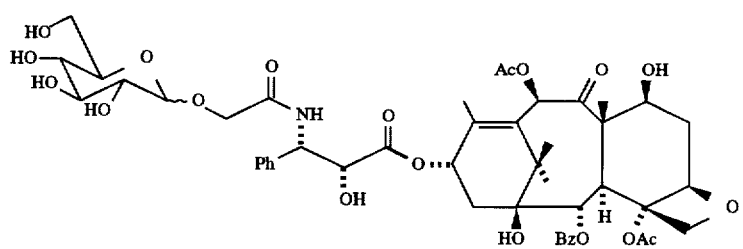

9. N-(glucosyloxyacetyl)-N-debutoxycarbonyldocetaxel represented by the following formula.

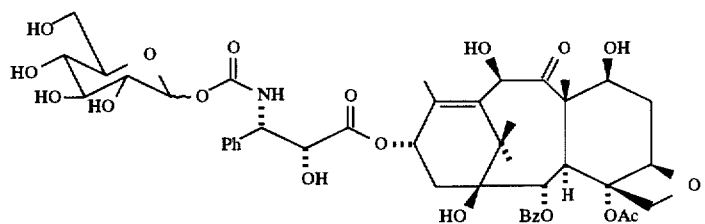

10. Glucosyloxyacetyl-2'-docetaxel represented by the following formula.

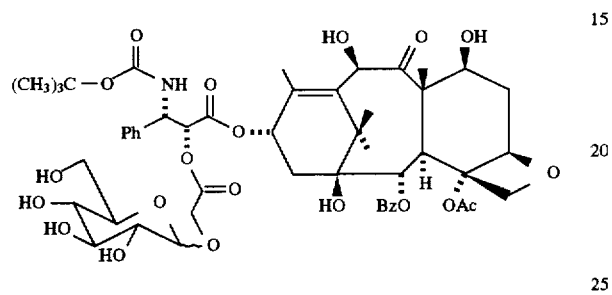

11. Diglucosyloxyacetyl-2',7-docetaxel represented by the following formula.

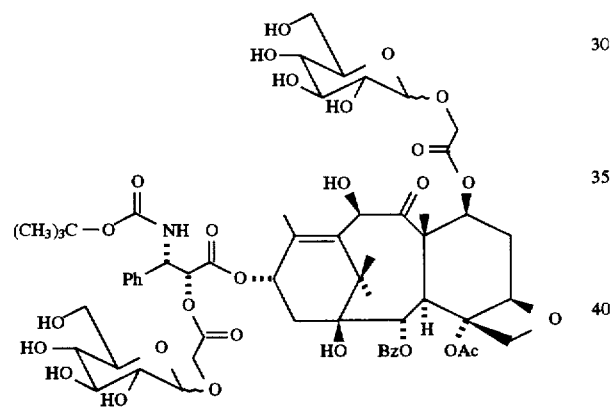

12. Triglucosyloxyacetyl-2',7,10-docetaxel represented by the following formula.

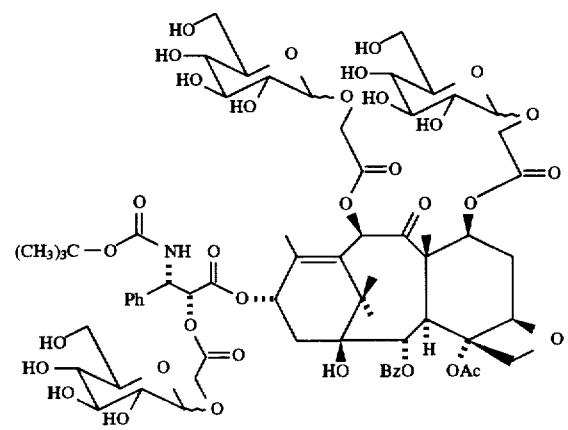

13. Glucosyloxyacetyl-7-docetaxel represented by the following formula.

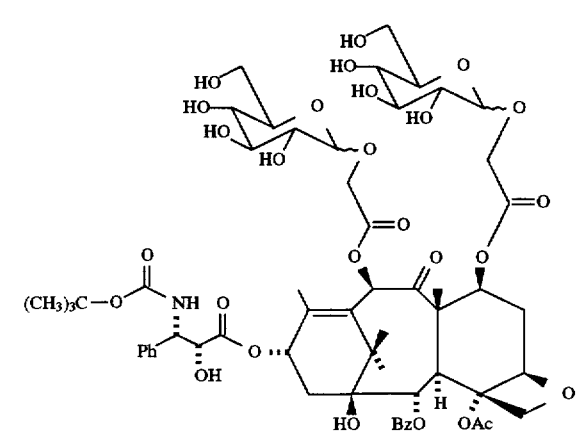

14. Diglucosyloxyacetyl-7,10-docetaxel represented by the following formula.

15. Glucosyloxyacetyl-10-docetaxel represented by the following formula.

16. Glucosyloxyacetyl-10-baccatin III represented by the following formula.

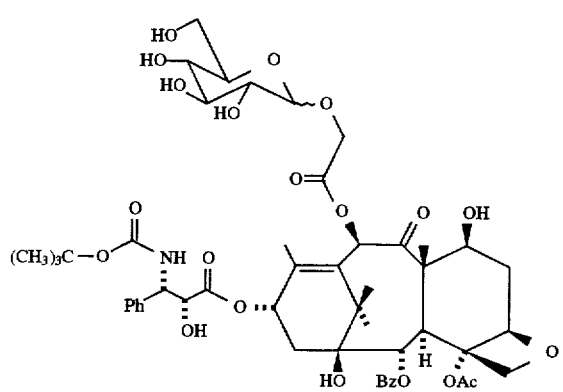

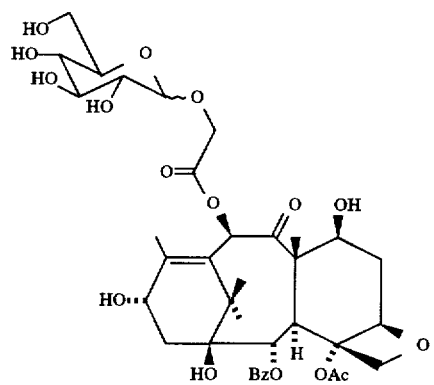

17. A method of producing a taxoid derivative of claim 4, 13 or 14, comprises protecting a hydroxyl group at the 2' position of a paclitaxel or docetaxel by chlorotriethylsilane followed by reacting said paclitaxel or docetaxel with tetrabenzyl acetyloxyglucoside represented by the following formula and then, carrying out debenzyl and detriethylsilyl reactions.

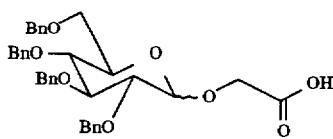

18. A method of producing a taxoid derivative of any one of claims 5, 6, 10, 11 and 12, comprises reacting paclitaxel or docetaxel with tetrabenzyl acetyloxyglucoside represented by the following formula and then, by carrying out a debenzyl reaction.

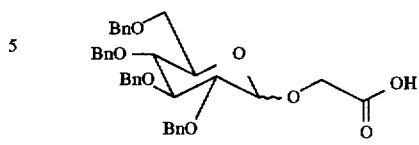

19. A method of producing a taxoid derivative of claim 15, comprises protecting hydroxyl groups at the 2' and 7 positions of docetaxel by triethylsilyl groups followed by reacting said docetaxel with tetrabenzyl acetyloxyglucoside represented by the following formula and then, carrying out debenzyl and detriethylsilyl reactions.

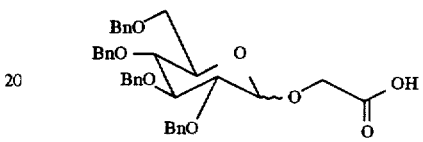

20. A method of producing a taxoid derivative of claim 7, comprises protecting hydroxyl groups at the 2' and 7 positions of 10-deacetylpaclitaxel by a triethylsilyl group, reacting said 10-deacetylpaclitaxel with tetrabenzyl acetyloxyglucoside represented by the following formula and then, carrying out debenzyl and detriethylsilyl reactions.

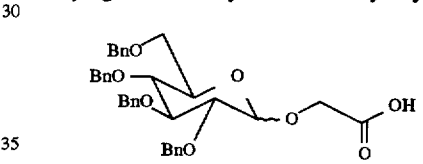

21. A method of producing a taxoid derivative of claim 16, comprises protecting hydroxyl groups at the 7 position of 10-deacetyl-baccatin III by a triethylsilyl group, reacting said 10-deacetylpaclitaxel with tetrabenzyl acetyloxyglucoside represented by the following formula and then, carrying out debenzyl and detriethylsilyl reactions.

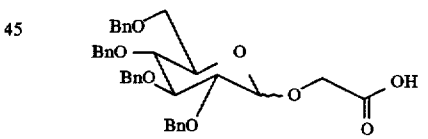

* * * * *